(12) United States Patent
Jordine et al.

(10) Patent No.: US 8,530,522 B2
(45) Date of Patent: Sep. 10, 2013

(54) ORGANIC COMPOUNDS

(75) Inventors: Guido Jordine, Freiburg (DE); Michael Mutz, Freiburg (DE)

(73) Assignee: Novartis AG, Basel (CH)

( * ) Notice: Subject to any disclaimer, the term of this patent is extended or adjusted under 35 U.S.C. 154(b) by 141 days.

(21) Appl. No.: 13/128,825

(22) PCT Filed: Nov. 10, 2009

(86) PCT No.: PCT/EP2009/064891
§ 371 (c)(1),
(2), (4) Date: May 20, 2011

(87) PCT Pub. No.: WO2010/055028
PCT Pub. Date: May 20, 2010

(65) Prior Publication Data
US 2011/0229501 A1    Sep. 22, 2011

(30) Foreign Application Priority Data

Nov. 11, 2008  (EP) ..................................... 08168865

(51) Int. Cl.
*A61K 31/137* (2006.01)
*C07C 215/28* (2006.01)
*A61P 37/06* (2006.01)

(52) U.S. Cl.
USPC .......................................... 514/653; 564/360

(58) Field of Classification Search
USPC .......................................... 514/653; 564/360
See application file for complete search history.

(56) References Cited

U.S. PATENT DOCUMENTS 5,604,229 A * 2/1997 Fujita et al. ................ 514/252.1
6,476,004 B1   11/2002 Sakai et al.

FOREIGN PATENT DOCUMENTS

| EP | 0 627 406 A1 | 12/1994 |
| WO | WO/2004/089341 A | 10/2004 |
| WO | 2012/041358 A1 | 4/2012 |

OTHER PUBLICATIONS

Kiuchi M et al. "Synthesis and Immunosuppressive Activity of 2-Substituted 2-Aminopropane-1,3-diols and 2-Aminoethanols" Journal of Medicinal Chemistry, American Chemical Soc., pp. 2946-2961. XP002271142, 2000.

"Disclosed Anonymously" "Solid State Forms of 2-amino-242-(4-octylphenypethy1]-1,3-propanediol hydrochloride." IP.com Journal, 2011, 11(12B), 19-20 (No. IPCOM000213350D).

* cited by examiner

*Primary Examiner* — Sreeni Padmanabhan
*Assistant Examiner* — Sahar Javanmard
(74) *Attorney, Agent, or Firm* — Andrew Holmes; Karen DeBenedictis

(57) ABSTRACT

The present invention relates to crystalline forms and hydrates of 2-Amino-2-[2-(4-$C_{2-20}$-alkyl-phenyl)ethyl]propane-1,3-diol, and to the use thereof, in particular in the treatment or prevention of various autoimmune conditions.

5 Claims, 4 Drawing Sheets

ORGANIC COMPOUNDS

The present invention relates to crystalline forms and hydrates of the compound FTY720 hydrochloride, and to the use thereof.

2-Amino-2-[2-(4-$C_{2-20}$-alkyl-phenyl)ethyl]propane-1,3-diol compounds are disclosed in EP-A-0627406, the relevant disclosure of which is incorporated herein by reference. On the basis of observed activity, the compounds have been found to be useful as immunosuppressants. Accordingly, the compounds may be useful in the treatment or prevention of various autoimmune conditions, including multiple sclerosis. A particular compound in this class is FTY720 (2-amino-2-[2-(4-octylphenyl)ethyl]propane-1,3-diol; fingolimod), which may be obtained in the form of the free base or a hydrochloride salt. The structure of FTY720 is shown below:

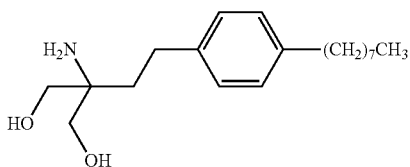

The present invention is based in part on a discovery that the FTY720 hydrochloride exhibits polymorphism. As the Examples given herein illustrate, FTY720 hydrochloride exists in a particular crystalline form (hereinafter Form I) at room temperature. Crystalline Form I undergoes a change to an alternative crystalline form (Form II) at a transition temperature of approximately 40° C. Moreover, crystalline Form II undergoes a transition to a third crystalline form (Form III) at a temperature of approximately 66° C. At a temperature of approximately 107° C., FTY720 hydrochloride forms a phase with lower crystalline order.

Accordingly, the present invention provides novel crystalline forms of FTY720 hydrochloride, including solvates, especially hydrates, thereof.

Crystalline Form I of FYT720 hydrochloride is characterised by an X-ray powder diffraction pattern having peaks at least two, preferably at least four, and more preferably all, of the following 2-theta values: 3.6, 7.1, 10.7, 12.5, 15.4 and 20.6 degrees 2-theta. The peaks at said 2-theta values may have the following relative intensities: 3.6 (strong), 7.1 (weak), 10.7 (weak), 12.5 (weak), 15.4 (medium) and 20.6 (medium).

In one embodiment this crystalline form is characterised by an X-ray powder diffraction pattern having peaks at least two preferably at least four, and more preferably all, of the following 2-theta values: 3.55, 7.12, 10.71, 12.48, 15.42 and 20.59 degrees 2-theta. The peaks at said 2-theta values may have the following relative intensities: 3.55 (strong), 7.12 (weak), 10.71 (weak), 12.48 (weak), 15.42 (medium) and 20.59 (medium).

Figure 1:
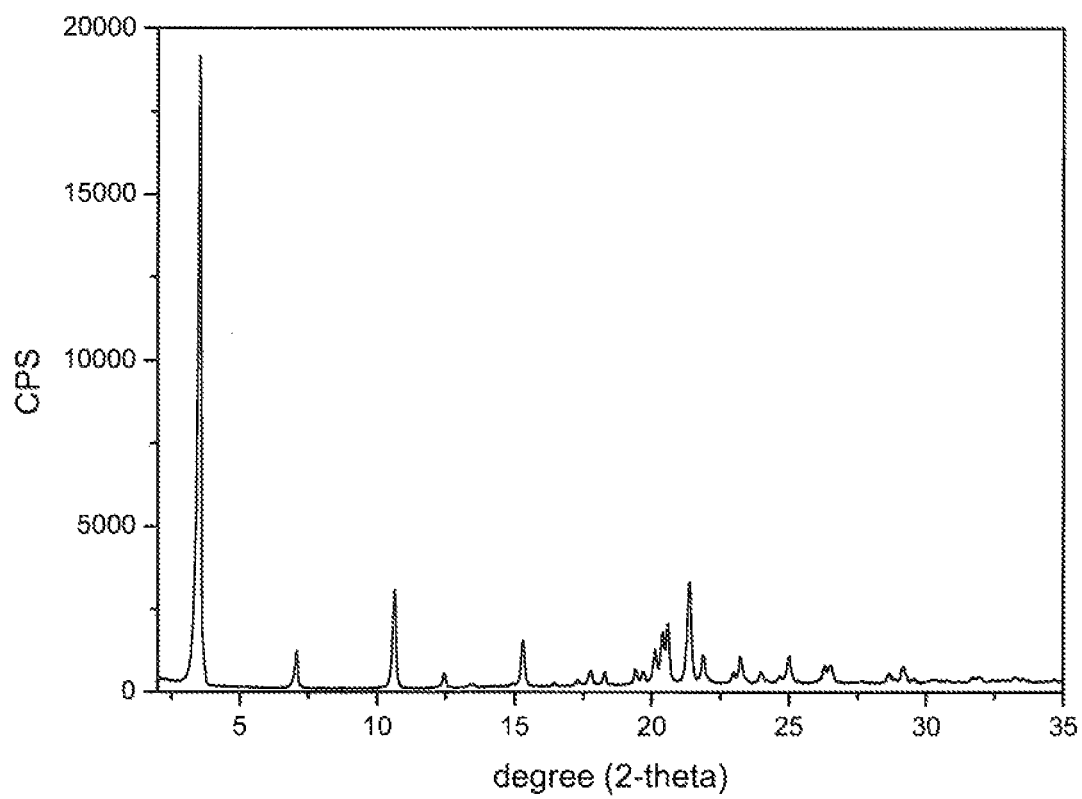

In a particular embodiment, this crystalline form is characterised by an X-ray powder diffraction pattern corresponding substantially to that shown in FIG. 1.

Crystalline (Form II) of FTY720 hydrochloride is characterised by an X-ray powder diffraction pattern having peaks at least two, preferably at least four, and more preferably all, of the following 2-theta values: 3.5, 6.9, 10.4, 14.6, 19.2, 20.3 and 20.9 degrees 2-theta. The peaks at said 2-theta values may have the following relative intensities: 3.5 (strong), 6.9 (weak), 10.4 (weak), 14.6 (weak), 19.2 (weak), 20.3 (weak) and 20.9 (weak).

In one embodiment this crystalline form is characterised by an X-ray powder diffraction pattern having peaks at least two, preferably at least four, and more preferably all, of the following 2-theta values: 3.47, 6.92, 10.38, 14.58, 19.20, 20.34 and 20.86 degrees 2-theta. The peaks at said 2-theta values may have the following relative intensities: 3.47 (strong), 6.92 (weak), 10.38 (weak), 14.58 (weak), 19.20 (weak), 20.34 (weak) and 20.86 (weak). In a particular embodiment, this crystalline form is characterised by an X-ray powder diffraction pattern corresponding substantially to that shown in FIG. 2.

Crystalline form (Form III) of FTY720 hydrochloride is characterised by an X-ray powder diffraction pattern having peaks at least two preferably at least four, and more preferably all of the following 2-theta values: 3.5, 6.9, 10.3, 14.4, 18.9, 20.3, 20.7 and 24.2 degrees 2-theta. The peaks at said 2-theta values may have the following relative intensities: 3.5 (strong), 6.9 (weak), 10.3 (weak), 14.4 (weak), 18.9 (weak), 20.3 (weak), 20.7 (weak) and 24.2 (weak).

In one embodiment this crystalline form is characterised by an X-ray powder diffraction pattern having peaks at least two, preferably at least four, and more preferably all, of the following 2-theta values: 3.46, 6.88, 10.32, 14.41, 18.94, 20.26, 20.73 and 24.23 degrees 2-theta. The peaks at said 2-theta values may have the following relative intensities: 3.46 (strong), 6.88 (weak), 10.32 (weak), 14.41 (weak), 18.94 (weak), 20.26 (weak), 20.73 (weak) and 24.23 (weak).

Figure 3:
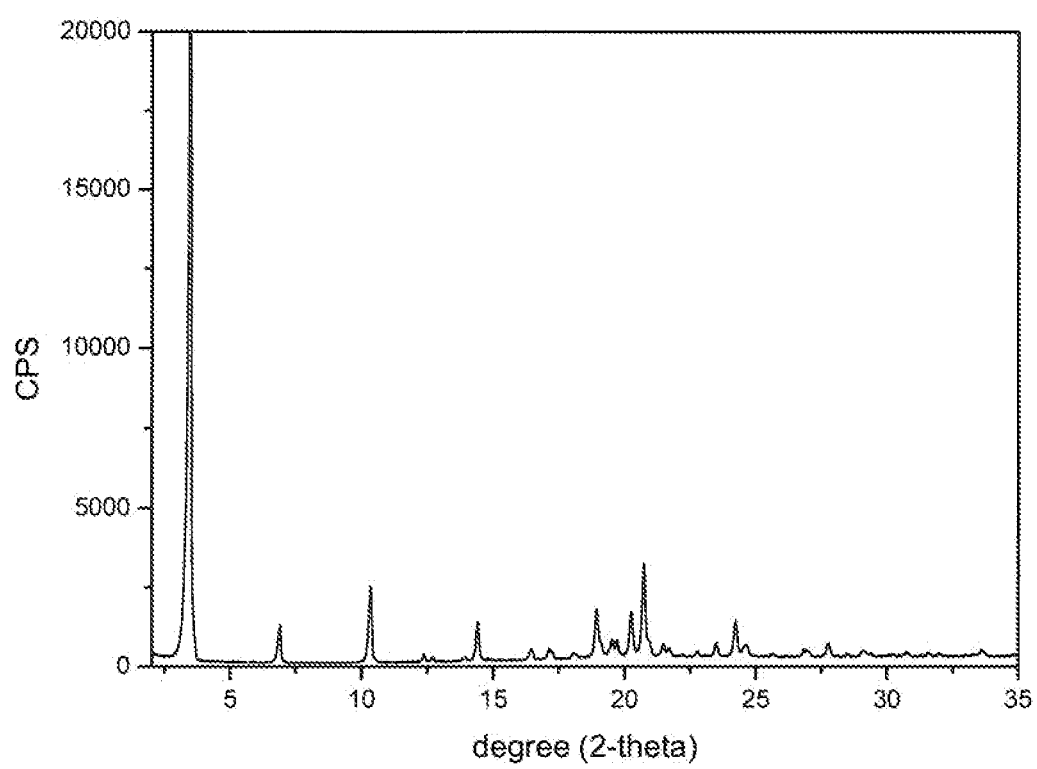

In a particular embodiment, this crystalline form is characterised by an X-ray powder diffraction pattern corresponding substantially to that shown in FIG. 3.

In addition, the invention provides a process for the production of crystalline Form I of FTY720 hydrochloride, which comprises cooling crystalline Form II or Form III of FTY720 hydrochloride to a temperature of less than 40° C. Preferably, the process comprises cooling to a temperature of 30° C. or less, more preferably 20° C. or less, more preferably still 10° C. or less, e.g. still 8° C. or less, e.g. 2 to 8° C., in order to ensure conversion to crystalline Form I.

It has also been found that FTY720 hydrochloride may exist substantially in the form of a hydrate. In an embodiment, the hydrate is characterised by an X-ray powder diffraction pattern having at least two, preferably at least four and more preferably all, peaks at about 2.9, 17.2, 30.6, 28.2, 24.4, 8.6 and 25.9 degrees 2-theta. The peaks at said 2-theta values may have the following relative intensities: 2.9 (strong), 17.2 (medium), 30.6 (weak), 28.2 (weak), 24.4 (weak), 8.6 (weak) and 25.9 (weak). In a particular embodiment, there is provided a hydrate of FTY720 hydrochloride characterised by an X-ray powder diffraction pattern corresponding substantially to that shown in FIG. 4.

By way of illustration, and without limitation, the various crystalline forms and hydrates of FTY720 hydrochloride may be obtained according to the procedures given in the Examples herein. In particular, interconversion between the various polymorphic forms of FYT720 hydrochloride may be achieved by heating or cooling FTY720 hydrochloride in accordance with the procedures described in the Examples.

Advantageously, the various crystalline salt forms of the invention may have one or more desirable properties compared with the free base form of FTY720. For example, crystalline salts of the invention may be more stable and of better quality than the free base, in particular during storage and distribution. In addition, the salts may have a high degree of dissociation in water and thus substantially improved water solubility. The salts may also be advantageous in that they show no measurable water absorption or loss.

Crystalline forms may be characterized by the major peaks of an X-ray powder diffraction spectrum, as illustrated in the Examples herein. Crystalline forms may also differ with respect to their thermodynamic stability, in their physical parameters, such as the absorption pattern in an infrared spectroscopy (IR) or phase transition signals in differential scanning calorimetry (DSC).

In an embodiment of the invention, the various crystalline salt forms of the present invention are in substantially pure crystalline form. The term "substantially pure" as used herein includes reference to crystalline forms of, or greater than, 90%, more preferably 95%, more preferably 96%, more preferably 97%, more preferably 98%, more preferably 99% polymorphic purity as determined, for example, by X-ray powder diffraction, Raman spectroscopy or IR spectroscopy.

Also provided are pharmaceutical formulations comprising a crystalline salt of the invention. A pharmaceutical formulation of the invention preferably contains 0.01 to 20% by weight of the salt, more preferably 0.1 to 10%, e.g. 0.5 to 5% by weight, based on the total weight of the formulation.

The pharmaceutical formulation may be a solid pharmaceutical composition in a form suitable for oral administration, e.g. a tablet or capsule. The composition may be manufactured in a conventional manner, e.g. by mixing a salt of the invention with a pharmaceutically acceptable carrier or diluent.

In a particular embodiment, the formulation is a solid pharmaceutical composition comprising a salt of the invention and a sugar alcohol. Compositions of this type are disclosed in WO 2004/089341, the contents of which are incorporated herein by reference. The solid compositions disclosed in this publication are particularly well suited to the oral administration of the salts of the present invention. The compositions provide a convenient means of systemic administration of the compounds, do not suffer from the disadvantages of liquid formulations for injection or oral use, and have good physicochemical and storage properties. In particular, the compositions of the present invention may show a high level of uniformity in the distribution of the compound throughout the composition, as well as high stability. The compositions may therefore be manufactured on high speed automated equipment, and thus do not require hand encapsulation.

The sugar alcohol may act as a diluent, carrier, filler or bulking agent, and may suitably be mannitol, maltitol, inositol, xylitol or lactitol, preferably a substantially non-hygroscopic sugar alcohol, e.g. mannitol (D-mannitol). A single sugar alcohol may be used or a mixture of two or more sugar alcohols, e.g a mixture of mannitol and xylitol, e.g. in a ratio of 1:1 to 4.1.

In a particularly preferred embodiment, the sugar alcohol is prepared from a spray-dried composition, e.g. mannitol composition, having a high specific surface area. The use of this type of mannitol composition may assist in promoting uniform distribution of the compound throughout the mannitol in the composition. A higher surface area may be achieved by providing a sugar alcohol, e.g. mannitol, preparation consisting of particles having a smaller mean size and/or a rougher surface on each particle. The use of a spray-dried sugar alcohol, e.g. mannitol, e.g. with a mean particle size of 300 μm or less, has also been found to improve compressibility and hardness of tablets formed from the composition.

Preferably the single point surface area of the sugar alcohol preparation, e.g. mannitol, is 1 to 7 $m^2/g$, e.g. 2 to 6 $m^2/g$ or 3 to 5 $m^2/g$. The mannitol preparation may suitably have a mean particle size of 100 to 300 μm, e.g. 150 to 250 μm and a bulk density of 0.4 to 0.6 g/mL, e.g. 0.45 to 0.55 g/mL. A suitable high surface area mannitol is Parteck M200, available commercially from E. Merck.

The composition preferably contains 75 to 99.99% by weight of the sugar alcohol, more preferably 85 to 99.9%, e.g. 90 to 99.5% by weight, based on the total weight of the composition.

The composition preferably further comprises a lubricant. Suitable lubricants include stearic acid, magnesium stearate, calcium stearate, zinc stearate, glyceryl palmitostearate, sodium stearyl fumarate, canola oil, hydrogenated vegetable oil such as hydrogenated castor oil (e.g Cutina® or Lubriwax® 101), mineral oil, sodium lauryl sulfate, magnesium oxide, colloidal silicon dioxide, silicone fluid, polyethylene glycol, polyvinyl alcohol, sodium benzoate, talc, poloxamer, or a mixture of any of the above. Preferably the lubricant comprises magnesium stearate, hydrogenated castor oil or mineral oil. Colloidal silicon dioxide and polyethylene glycol are less preferred as the lubricant.

The composition preferably contains 0.01 to 5% by weight of a lubricant, more preferably 1 to 3% by weight, e.g. about 2% by weight based on the total weight of the composition.

The composition may comprise one or more further excipients such as carriers, binders or diluents. In particular, the composition may comprise microcrystalline cellulose (e.g. Avicel®), methylcellulose, hydroxypropylcellulose, hydroxypropylmethylcellulose, starch (e.g corn starch) or dicalcium phosphate, preferably in an amount of from 0.1 to 90% by weight, e.g. 1 to 30% by weight, based on the total weight of the composition. Where a binder, e.g microcrystalline cellulose, methylcellulose, hydroxypropyl cellulose, hydroxypropylmethyl cellulose is used it is preferably included in an amount of 1 to 8%, e.g. 3 to 6% by weight, based on the total weight of the composition. The use of a binder increases the granule strength of the formulation, which is particularly important for fine granulations. Microcrystalline cellulose and methylcellulose are particularly preferred where a high tablet hardness and/or longer disintegration time is required. Hydroxypropyl cellulose is preferred where faster disintegration is required. Where appropriate, xylitol may also be added as an additional binder, for example in addition to microcrystalline cellulose, e.g. in an amount up to 20% by weight of the sugar alcohol, e.g. xylitol.

In one embodiment, the composition further comprises a stabiliser, preferably glycine HCl or sodium bicarbonate. The stabiliser may be present in an amount of e.g. 0.1 to 30%, preferably 1 to 20% by weight.

The composition may be in the form of a powder, granule or pellets or a unit dosage form, for example as a tablet or capsule. The compositions of the present invention are well-adapted for encapsulation into an orally administrable capsule shell, particularly a hard gelatin shell.

Alternatively the compositions may be compacted into tablets. The tablets may optionally be coated, for instance with talc or a polysaccharide (e.g. cellulose) or hydroxypropylmethylcellulose coating.

Where a pharmaceutical capsule is in unit dosage form, each unit dosage may, for example, contain from about 0.5 to about 10 mg of a salt of the invention.

The compositions of the invention may show good stability characteristics as indicated by standard stability trials, for example having a shelf life stability of up to one two or three years, and even longer. Stability characteristics may be determined, e.g. by measuring decomposition products by HPLC analysis after storage for particular times at particular temperatures, e.g. 20, 40 or 60° C.

The pharmaceutical compositions of the present invention may be produced by standard processes, for instance by conventional mixing, granulating, sugar-coating, dissolving or lyophilizing processes. Procedures which may be used are known in the art, e.g. those described. In L. Lachman at al. The Theory and Practice of Industrial Pharmacy, 3rd Ed, 1986, H Sucker et al, Pharmazeutische Technologie, Thiene, 1991, Hagers Handbuch der pharmazeutischen Praxis, 4th Ed. (SpringerVerlag, 1971) and Remington's Pharmaceutical Sciences, 13th Ed., (Mack Publ., Co., 1970) or later editions.

In an embodiment, the pharmaceutical composition is produced by a process comprising:
(a) mixing a salt of the invention with a sugar alcohol;
(b) milling and/or granulating the mixture obtained in (a); and
(c) mixing the milled and/or granulated mixture obtained in (b) with a lubricant.

By using this process, a preparation having a good level of content and blend uniformity (i.e. a substantially uniform distribution of the salt throughout the composition), dissolution time and stability is obtained.

The salt may optionally be micronized, and/or pre-screened, e.g. with a 400 to 500 μm mesh screen, before step (a) in order to remove lumps. The mixing step (a) may suitably comprise blending the salt and the sugar alcohol, e.g. mannitol in any suitable blender or mixer for e.g. 100 to 400 revolutions.

The process may be carried out by dry mixing the components. In this embodiment the milling step (b) may suitably comprise passing the mixture obtained in (a) through a screen, which preferably has a mesh size of 400 to 500 μm. Process step (a) may comprise the step of mixing the total amount of the salt at first with a low amount of sugar alcohol, e.g. from 5 to 25% by weight of the total weight of sugar alcohol, in order to form a pre-mix.

Subsequently the remaining amount of sugar alcohol is added to the pre-mix. Step (a) may also comprise the step of adding a binder solution, e.g. methylcellulose and/or xylitol, e.g. an aqueous solution, to the mixture. Alternatively the binder is added to the mix dry and water is added in the granulation step.

The milled mixture obtained in (b) may optionally be blended once more before mixing with the lubricant. The lubricant, e.g. magnesium stearate, is preferably pre-screened, e.g. with a 800 to 900 μm screen, before mixing.

Alternatively, a wet granulation process is employed. In this embodiment, the salt is preferably first dry-mixed with the desired sugar alcohol, e.g. mannitol, and the obtained sugar alcohol/salt mixture is then dry-mixed with a binder such as hydroxypropyl cellulose or hydroxypropylmethyl cellulose. Water is then added and the mixture granulated, e.g. using an automated granulator. The granulation is then dried and milled.

If desirable, an additional amount of binder may be added in step (c) to the mixture obtained in (b).

The process may comprise a further step of tabletting or encapsulating the mixture obtained in (c), e.g. into a hard gelatin capsule using an automated encapsulation device. The capsules may be coloured or marked so as to impart an individual appearance and to make them instantly recognizable. The use of dyes can serve to enhance the appearance as well as to identify the capsules. Dyes suitable for use in pharmacy typically include carotenoids, iron oxides, and chlorophyll. Preferably, the capsules of the invention are marked using a code.

Salts and polymorphs of the invention may be useful in:
a) treatment and prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells; and
b) treatment and prevention of autoimmune disease or of inflammatory conditions, e.g. rheumatoid arthritis, systemic lupus erythematosus, hashimoto's thyroiditis, multiple sclerosis, myasthenia gravis, diabetes type I or II and the disorders associated therewith, vasculitis, pernicious anemia, Sjoegren syndrome, uveitis, psoriasis. Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis.

For the above uses the required dosage will of course vary depending on the mode of administration, the particular condition to be treated and the effect desired. In general, satisfactory results are indicated to be obtained at daily dosages of from about 0.1 to about 100 mg/kg body weight. An indicated daily dosage in the larger mammal, e.g. humans, is in the range of from about 0.5 mg to 2000 mg, conveniently administered, for example, in divided doses up to four times a day or in retard form.

The salts may be administered by any appropriate route, e.g. orally, for example in the form of a tablet or capsule, topically or parenterally, for example intravenously. Pharmaceutical compositions comprising a salt of the invention in association with at least one pharmaceutically acceptable carrier or diluent may be manufactured in conventional manner by mixing with a pharmaceutically acceptable earner or diluent. Unit dosage forms for oral administration contain, for example, from about 0.1 mg to about 500 mg of active substance.

The salts may be administered as the sole active ingredient or together with other drugs in immunomodulating regimens or other anti-inflammatory agents e.g. for the treatment or prevention of allograft acute or chronic rejection or inflammatory or autoimmune disorders. For example, they may be used in combination with calcineurin inhibitors, e.g. cyclosporin A, cyclosporin G, FK-506, ABT-281, ASM 981; an mTOR inhibitor, e.g. rapamycin, 40-O-(2-hydroxy)ethyl-rapamycin, CCI779, ABT578 or AP23573 etc.; corticosteroids; cyclophosphamide; azathioprene; methotrexate; another S1P receptor agonist, e.g. FTY 720 or an analogue thereof; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists.

Where a salt is administered in conjunction with another immunomodulating or anti-inflammatory agent, dosages of the co-administered immunomodulating or anti-inflammatory agent will of course vary depending on the type of co-drug employed, on the condition to be treated and so forth.

The present invention thus provides:
1. A method of treating or preventing organ or tissue transplant rejection, comprising administering to a subject a therapeutically effective amount of a crystalline salt of the invention.
2. A method of treating or preventing an autoimmune disease or inflammatory condition, comprising administering to a subject a therapeutically effective amount of a crystalline salt of the invention.
3. A crystalline salt of the invention for use as a pharmaceutical.
4. A pharmaceutical composition comprising a crystalline salt of the invention and a pharmaceutically acceptable diluent or carrier.
5. Use of a crystalline salt of the invention for the preparation of a medicament, e.g. in a method as disclosed above.
6. A pharmaceutical combination comprising (a) a crystalline salt of the invention and (b) a second drug substance, said second drug substance being suitable for the prevention or treatment of a condition described above.
7. A method as defined above comprising co-administration, e.g. concomitantly or in sequence, of (a) a crystalline salt of the invention and (b) a second drug substance, said second drug substance being suitable for the prevention or treatment of a condition described above.

The following Examples illustrate the invention. In Examples 1 to 13, references to Compound A, FTY720 or FTY720 hydrochloride salt should be taken to include reference to any of the various crystalline salt forms of the present invention.

EXAMPLE 1

Micronized Compound A, e 2-amino-2-[2-(4-octylphenyl) ethyl]propane-1,3-diol hydrochloride salt (FTY720), is screened and 116.7 g of the screened compound is mixed with 9683.3 g of a microcrystalline cellulose agent. The mixture is then milled in a Frewitt MGI device (Key International Inc. USA) using a 30 mesh screen. Magnesium stearate is screened using a 20 mesh screen and 200 g of the screened compound blended with the FTY720 mixture to produce a product composition.

The product composition is then compacted on a tablet press using a 7 mm die to form 120 mg tablets, each containing:

| | |
|---|---|
| Compound A, e.g. FTY720* | 1.4 mg |
| Microcrystalline cellulose, e.g. Avicel PH 102 | 116.2 mg |
| Magnesium stearate | 2.4 mg |
| Total | 120 mg |

*1 mg of Compound A in free form is equivalent to 1.12 mg of FTY720.

EXAMPLE 2

In a further example, the process of example 1 is repeated except that the magnesium stearate is replaced by Cutina® (hydrogenated castor oil).

EXAMPLE 3

Compound A, e.g. FTY720, and Microcrystalline cellulose, e.g. Avicel PH 102 are each screened separately using an 18 mesh screen. 1.9 g screened FTY720 is mixed with 40 g screened microcrystalline cellulose agent for 120 revolutions in a blender at 32 rpm. The FTY720 mixture is then screened through a 35 mesh screen.

The screened FTY720 mixture is added to a granulator along with a further 340.1 g Microcrystalline cellulose, e.g. Avicel PH 102 and 12 g hydroxypropylcellulose. The mixture is mixed for 3 minutes. Water is then added at a rate of 100 ml/minute and the mixture granulated for 2 minutes. The granulation is transferred into a tray dryer and dried at 50° C. for 150 minutes.

The mixture is then milled in a Frewitt MGI device using a 35 mesh screen. Magnesium stearate is screened and 6 g of the screened compound is blended for 90 revolutions at 32 rpm with the FTY720 mixture to produce a product composition showing a substantially uniform distribution of the S1P receptor agonist throughout the Microcrystalline cellulose, e.g. Avicel PH 102 in the blend.

The product composition is then filled into size 3 hard gelatin shells on an H & K 400 encapsulation device. 120 mg of the product composition is added to each capsule. Therefore each capsule contains:

| | |
|---|---|
| FTY720* | 0.56 mg |
| Miorocrystalline cellulose | 114.04 mg |
| Hydroxypropylcellulose | 3.6 mg |
| Magnesium stearate | 1.8 mg |
| Total | 120 mg |

EXAMPLE 4

In a further example, the process of example 3 is repeated except that the magnesium stearate is replaced by Cutina® (hydrogenated castor oil).

EXAMPLE 5

In a further example, the process of example 3 is repeated except that the hydroxypropyl cellulose is replaced by hydroxypropylmethyl cellulose.

EXAMPLE 6a

Micronized Compound A, e.g. FTY720, is screened using a 400 μm (40 mesh) screen. 58.35 g of the screened compound is mixed with 4841.65 g Microcrystalline cellulose, e.g. Avicel PH 102 in a 25 L Bohle bin blender for 240 blending revolutions. The mixture is then milled in a Frewitt MGI device using a 425 μm mesh screen, and the milled mixture is blended once more. Magnesium stearate is screened and 100 g of the screened compound is blended with the FTY720 mixture to produce a product composition showing a substantially uniform distribution of the SIP receptor agonist throughout the blend.

The product composition is then filled into size 3 hard gelatin shells on an H & K 400 encapsulation device. 120 mg of the product composition is added to each capsule. Therefore each capsule contains:

| | |
|---|---|
| FTY720* | 1.4 mg |
| Microcrystalline cellulose | 116.2 mg |
| Magnesium stearate | 2.4 mg |
| Total | 120 mg |

EXAMPLE 6b

In an alternative embodiment, capsules are manufactured using the components and in the amounts described in Example 6a, but the FTY720 is first mixed with 14 mg mannitol (before screening). This mixture is then screened as described above. The screened mixture is then blended with the remaining mannitol and the magnesium stearate is added, followed by additional blending and filling into capsules.

EXAMPLES 7 AND 8

In further examples, capsules are prepared as described in example 6, except that each capsule contains each component in the following amounts:

| | Example 7 | Example 8 |
|---|---|---|
| FTY720* | 2.8 mg | 5.6 mg |
| Microcrystalline cellulose | 114.8 mg | 112 mg |
| Magnesium stearate | 2.4 mg | 24 mg |
| Total | 120 mg | 120 mg |

EXAMPLES 9 TO 11

In further examples, capsules are prepared as described in examples 6 to 8, except that the magnesium stearate is replaced in each case by Cutina® (hydrogenated castor oil).

EXAMPLES 12 AND 13

Capsules containing the following ingredients are prepared, by weighing each component and mixing in a mortar, then filling into capsules:

| | Example 12 | Example 13 |
|---|---|---|
| FTY720 | 5 mg | 1 mg |
| D-mannitol | 83.7 mg | 117 mg |
| Corn starch | 24 mg | — |
| Avicel ® PH101 | 12 mg | — |
| Hydroxypropylcellulose | 0.3 mg | 7 mg |
| Talc | 3 mg | 3 mg |
| Lubri wax ® 101 | 2 mg | 2 mg |
| Total | 130 mg | 130 mg |

EXAMPLE 14

Polymorphs and Hydrates of FTY720 HCl

Differential scanning calorimetry (DSC) curves were recorded using the PerkinElmer DSC-7 and Pyris 1 system.

DSC heating curves showed three characteristic transitions at approximately 40° C., 66° C. and 107° C. The first endothermic peak at 40° C. is followed by a small exothermic peak which hints to melting of Form I followed by recrystallization into Form II. The second transition between Form II and Form III is a solid-solid transition. A third transition was observed at 107° C. Above 107° C., the X-ray powder pattern almost disappeared and only a single strong peak at 2.9° remained, suggesting formation of a phase with lower crystalline order above this temperature. Thermomicroscopy showed birefringence above 107° C. which disappeared only at ca. 230° C., which is below the onset of decomposition at ca. 260° C.

Variable temperature XRPD was then performed in order to investigate the nature of the different transitions seen in DSC. The heating rate was 10K/min and the stage time was min for each experiment X-ray powder diagrams were recorded between 2° and 35° (2 theta) with Cu Kα radiation using a Scintag X1 diffraction system. Temperature variable and humidity variable XRPD was performed using the Scintag XDS 2000 system equipped with a temperature and humidity control unit.

According to the variable-temperature XRPD, FTY720 HCl can exist in at least four different crystalline forms. Above 107° C. practically all diffraction peaks disappeared and only a single strong peak at 2.9° remained. These findings are in agreement with DSC results. However, a further crystalline form (Form IV) which was seen at 0° C. was only observed by XRPD and did not show up in DSC. As the X-ray powder pattern of Form IV was very similar to that of Form I and no thermal event was observed in DSC, it can be assumed that the crystal properties of Form IV are very similar to Form I.

The XRPD diagram of FTY720 hydrochloride Form I is shown in FIG. 1, with significant peaks given below:

| ° deg 2 θ | d-space (Å) | Relative intensity |
|---|---|---|
| 3.55 | 24.875 | Strong |
| 7.12 | 12.394 | Weak |
| 10.71 | 8.255 | Weak |
| 12.48 | 7.090 | Weak |
| 15.42 | 5.742 | Medium |
| 20.59 | 4.309 | Medium |

In a specific embodiment, the XRPD diagram of FTY720 hydrochloride Form I is:

| ° deg 2 θ | d-space | Relative intensity (%) |
|---|---|---|
| 3.55 | 24.875 | 100 |
| 7.12 | 12.394 | 4 |
| 10.71 | 8.255 | 10 |
| 12.48 | 7.090 | 7 |
| 15.42 | 5.742 | 15 |
| 20.59 | 4.309 | 20 |

Figure 2:
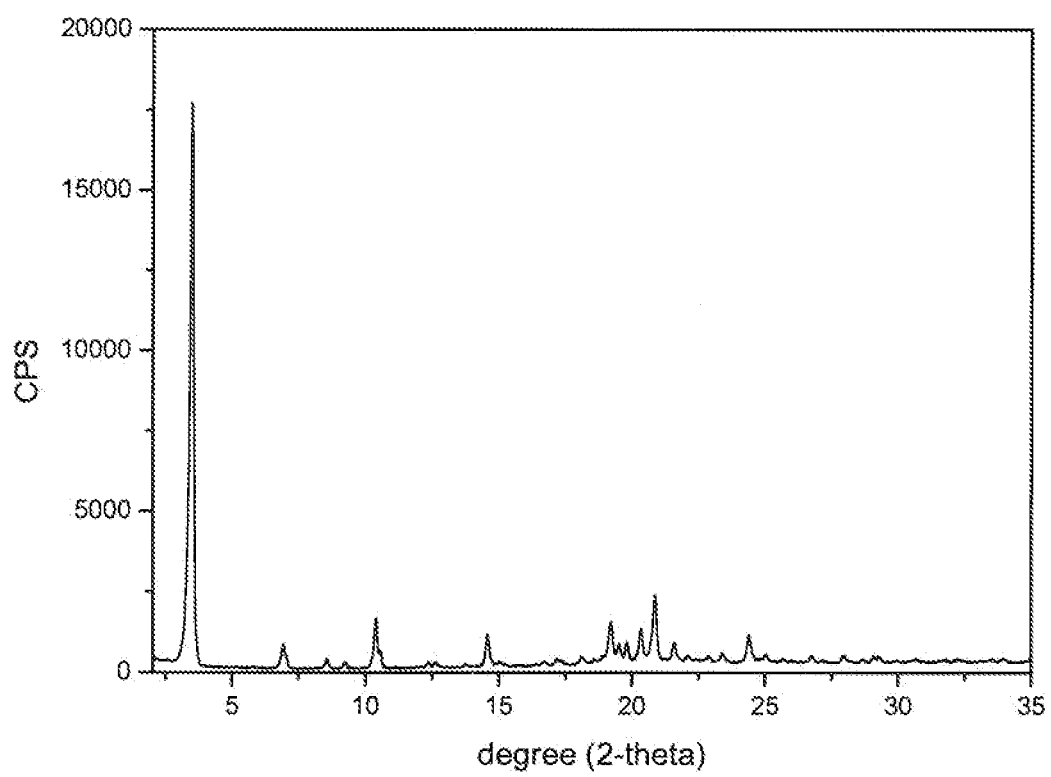

The XRPD diagram of FTY720 hydrochloride Form II is shown in FIG. 2, with significant peaks given below:

| ° deg 2 θ | d-space (Å) | Relative intensity |
|---|---|---|
| 3.47 | 25.467 | Strong |
| 6.92 | 12.756 | Weak |
| 10.38 | 8.513 | Weak |
| 14.58 | 6.070 | Weak |

-continued

| ° deg 2 θ | d-space (Å) | Relative intensity |
|---|---|---|
| 19.20 | 4.617 | Weak |
| 20.34 | 4.362 | Weak |
| 20.86 | 4.254 | Weak |

In a specific embodiment, the XRPD diagram of FTY720 hydrochloride Form II is:

| ° deg 2 θ | d-pace | Relative intensity (%) |
|---|---|---|
| 3.47 | 25.467 | 100 |
| 6.92 | 12.756 | 5 |
| 10.38 | 8.513 | 9 |
| 14.58 | 6.070 | 6 |
| 19.20 | 4.617 | 9 |
| 20.34 | 4.362 | 8 |
| 20.86 | 4.254 | 13 |

The XRPD diagram of FTY720 hydrochloride Form III is shown in FIG. 3, with significant peaks given below:

| ° deg 2 θ | d-space (Å) | Relative intensity |
|---|---|---|
| 3.46 | 25.467 | Strong |
| 6.88 | 12.826 | Weak |
| 10.32 | 8.559 | Weak |
| 14.41 | 6.138 | Weak |
| 18.94 | 4.679 | Weak |
| 20.26 | 4.378 | Weak |
| 20.73 | 4.279 | Weak |
| 24.23 | 3.668 | Weak |

In a specific embodiment, the XRPD diagram of FTY720 hydrochloride Form II is:

| ° deg 2 θ | d-space | Relative intensity (%) |
|---|---|---|
| 3.46 | 25.467 | 100 |
| 6.88 | 12.826 | 6 |
| 10.32 | 8.559 | 11 |
| 14.41 | 6.138 | 6 |
| 18.94 | 4.679 | 8 |
| 20.26 | 4.378 | 7 |
| 20.73 | 4.279 | 14 |
| 24.23 | 3.668 | 6 |

Some margin of error, of approximately ±0.2 deg may be present in each of the 2 θ angle assignments.

Sorption/desorption isotherms were measured using the Dynamic Vapor System (DVS-1). Measurement was carried out at 25° C. and 40° C.

A water desorption isotherm recorded at 25° C. showed between 90% and 60% relative humidity (r.h.) a nearly constant water content of 5.2 to 5.9%. This suggests the formation of a hydrate (theoretical water content of a monohydrate is 4.98%). The water sorption isotherm recorded at 40° C. showed a first significant water uptake already at 80% r.h., whereas the isotherm recorded at 25° C. showed the first uptake at 90% r.h. Samples of Form I stored for 1 month at 60° C. and 75% r.h. and 1 month at 80° C. and 75% r.h. show conversion to the hydrate form with water contents of 10.2 to 10.6%, which is close to the calculated water content of 9.48% for two moles of water).

Figure 4:
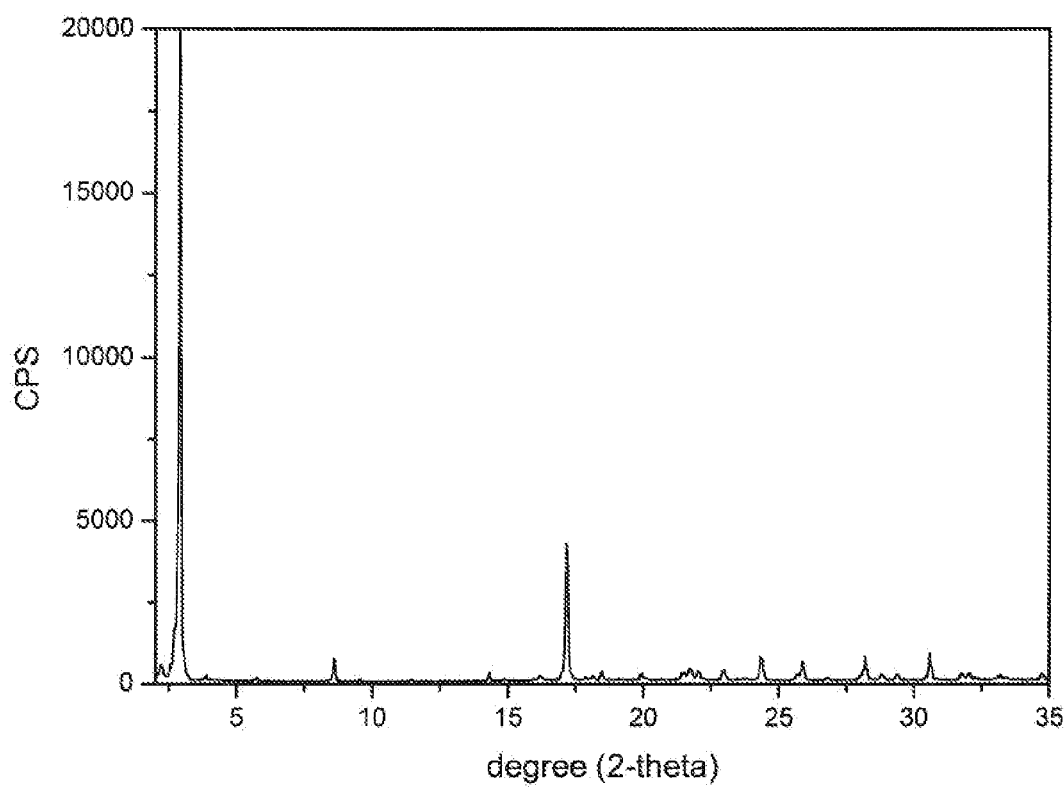

The XRPD diagram of the hydrate is shown in FIG. 4, with significant peaks given below:

| ° deg 2 θ | d-space (Å) | Relative intensity |
|---|---|---|
| 2.9 | 30.298 | Strong |
| 17.2 | 5.160 | Medium |
| 30.6 | 2.921 | Weak |
| 28.2 | 3.161 | Weak |
| 24.4 | 3.651 | Weak |
| 8.6 | 10.280 | Weak |
| 25.9 | 3.438 | Weak |

In a specific embodiment of the invention, the XRPD diagram of the hydrate is

| ° deg 2 θ | d-space | Relative Intensity (%) |
|---|---|---|
| 2.9 | 30.298 | 100 |
| 17.2 | 5.160 | 26 |
| 30.6 | 2.921 | 6 |
| 28.2 | 3.161 | 5 |
| 24.4 | 3.651 | 4 |
| 8.6 | 10.280 | 4 |
| 25.9 | 3.438 | 4 |

The invention claimed is:

1. A pharmaceutical composition comprising a hydrate of the hydrochloride salt of 2-amino-2-(2-(4-octylphenyl)ethyl)propane-1,3-diol (FTY720) in crystalline form, wherein said crystalline hydrate is characterised by an X-ray powder diffraction pattern with peaks at about 2.9, 17.2, 30.6, 28.2, 24.4, 8.6 and 25.9 degrees 2-theta.

2. A composition according to claim 1, wherein the water content is from 5.2 to 10.6%.

3. A composition of claim 1, for use in therapy.

4. A composition of claim 1, for use in the treatment of organ or tissue transplant rejection, autoimmune diseases or inflammatory conditions.

5. A hydrate of the hydrochloride salt of 2-amino-2-(2-(4-octylphenyl)ethyl)propane-1,3-diol in crystalline form, wherein said crystalline hydrate is characterised by an X-ray powder diffraction pattern with peaks at about 2.9, 17.2, 30.6, 28.2, 24.4, 8.6 and 25.9 degrees 2-theta.

* * * * *